United States Patent
Mizutani (12)

(10) Patent No.: US 6,410,822 B1
(45) Date of Patent: Jun. 25, 2002

(54) SANITARY NAPKIN HAVING ELASTIC MEMBER THAT LIFTS UPPER PORTION THEREOF

(75) Inventor: Satoshi Mizutani, Kagawa-ken (JP)

(73) Assignee: Uni-Charm Corporation (JP)

(*) Notice: Subject to any disclaimer, the term of this patent is extended or adjusted under 35 U.S.C. 154(b) by 0 days.

(21) Appl. No.: 09/396,676

(22) Filed: Sep. 9, 1999

(30) Foreign Application Priority Data

Sep. 11, 1998 (JP) .......................................... 10-257977

(51) Int. Cl.⁷ .......................... A61F 13/15; A61F 13/20
(52) U.S. Cl. .............................. 604/380; 604/385.101; 604/385.01
(58) Field of Search ................................ 604/379, 380, 604/385.01, 385.26, 385.27, 385.101, 385.17, 385.19, 385.24, 385.25, 385.28, 385.29

(56) References Cited

U.S. PATENT DOCUMENTS

| 3,575,174 A | | 4/1971 | Mogor | |
|---|---|---|---|---|
| 4,808,177 A | * | 2/1989 | DesMarais et al. | 604/385.1 |
| 4,935,021 A | * | 6/1990 | Huffman et al. | 604/385.1 |
| 5,236,428 A | * | 8/1993 | Zajaczkowski | 604/385.2 |
| 5,674,341 A | | 10/1997 | Ng | |
| 5,704,928 A | * | 1/1998 | Morita et al. | 604/385.1 |
| 5,795,345 A | * | 8/1998 | Mizutani et al. | 604/380 |
| 5,899,894 A | * | 5/1999 | Palumbo et al. | 604/378 |
| 6,152,908 A | * | 11/2000 | Widlund | 604/385.19 |

FOREIGN PATENT DOCUMENTS

| EP | 0 769 284 | 4/1997 |
|---|---|---|
| EP | 0 904 755 | 3/1999 |
| JP | 2527597 | 11/1996 |
| WO | WO 95/17148 | 6/1995 |
| WO | WO 97/07763 | 3/1997 |

OTHER PUBLICATIONS

Copy of European Search Report mailed Nov. 9, 2001.

* cited by examiner

*Primary Examiner*—John G. Weiss
*Assistant Examiner*—Michele Kidwell
(74) *Attorney, Agent, or Firm*—Baker & Daniels

(57) ABSTRACT

A sanitary napkin including therein an elastic member longitudinally extending under tension along a center line dividing a width of the napkin. An upper portion of the napkin protrudes upward as the elastic member contracts. In the vicinity of both side edges of the napkin, topsheet is compressed together with absorbent core underlying the topsheet toward a backsheet to form a pair of compressed grooves extending longitudinally of the napkin.

6 Claims, 2 Drawing Sheets

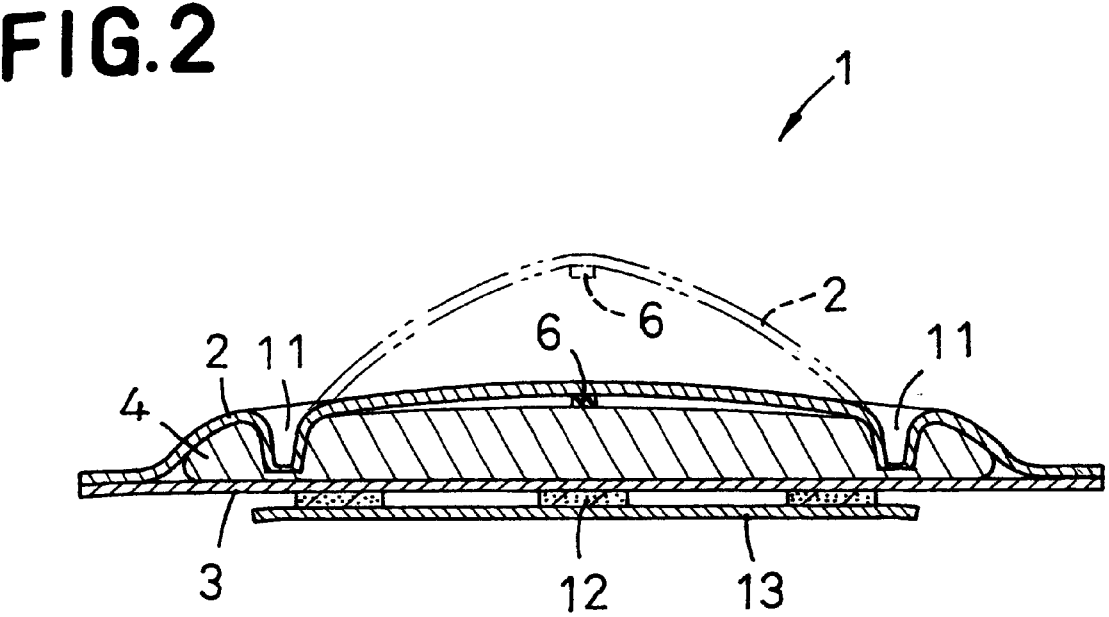
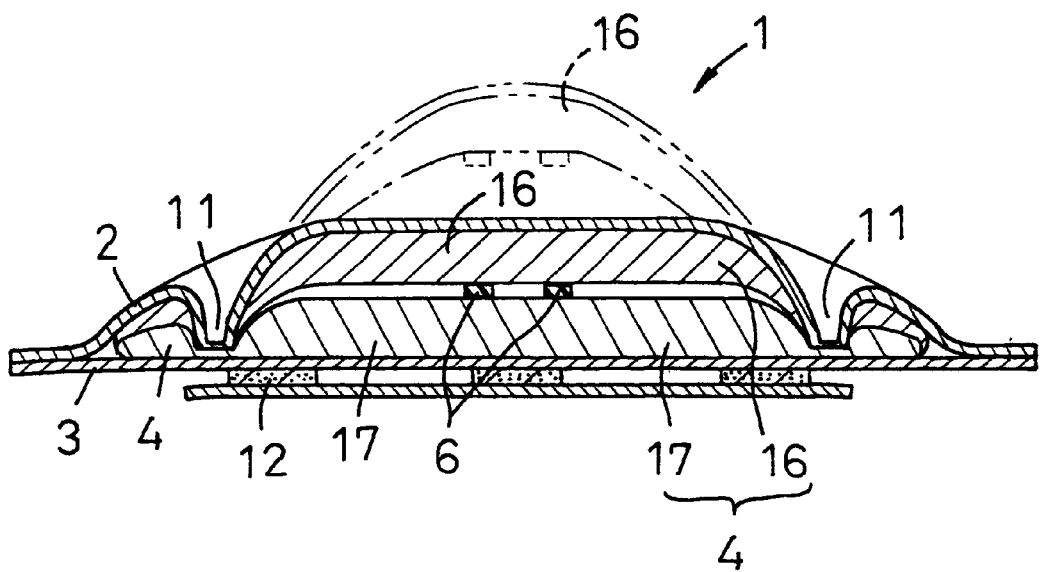

SANITARY NAPKIN HAVING ELASTIC MEMBER THAT LIFTS UPPER PORTION THEREOF

BACKGROUND OF THE INVENTION

This invention relates to a sanitary napkin for absorption and containment of menstrual discharge.

Japanese Utility Model Registration No. 2527597 discloses a sanitary napkin provided in its longitudinally middle region under an upper layer portion of the napkin with an elastic member adapted to be stretched and contracted longitudinally of the napkin. A portion of a topsheet overlying the elastic member protrudes when the napkin is put on a wearer's body and thereupon the elastic member contracts. As a result, the protruding portion of the napkin comes in close contact with the wearer's pudendum.

In the case of the known sanitary napkin, most of menstrual discharge is absorbed through the protruding portion of the topsheet but any excessive amount of menstrual discharge will flow down laterally along a sloped surface of the protruding portion of the topsheet and may cause undesirable sideways leakage.

SUMMARY OF THE INVENTION

It is an object of this invention to, in a napkin having its longitudinally middle region adapted to protrude, prevent, menstrual discharge from leaking sideways.

A sanitary napkin according to the invention includes a liquid-pervious topsheet, a liquid-impervious backsheet and a liquid-absorbent core disposed between said topsheet and backsheet.

The sanitary napkin further includes the following arrangements: Between the topsheet and the backsheet, at least a single elastic member extending longitudinally under tension and having longitudinally opposite ends bonded to one of the topsheet and the backsheet so that the elastic member is stretched and contracted between the ends. In the vicinity of transversely opposite side edges of said napkin, said topsheet is compressed together with the absorbent core underlying the topsheet toward the backsheet to form a pair of compressed grooves extending longitudinally of the napkin. The topsheet and the backsheet and the absorbent core are integrated so that they are not easily separable one from another in the grooves and portions of the napkin lying in the grooves have a density higher than a density of the napkin in the vicinity of the grooves. Between the pair of grooves, a portion of the napkin overlying the elastic member in a thickness direction of the napkin is formed separably from a portion of the napkin underlying the elastic member also in the thickness direction of the napkin so that the portion of the napkin overlying the elastic member moves upward as the napkin is longitudinally curved with the topsheet lying inside and thereupon the elastic member contracts.

According to one embodiment of this invention, the elastic member is disposed between the topsheet and the absorbent core.

According to another embodiment of this invention, the absorbent core comprises an upper layer portion and a lower layer portion between which the elastic member is disposed between these two layer portions.

BRIEF DESCRIPTION OF THE DRAWINGS

FIG. 2 is a sectional view taken along a line II—II in FIG. 1; and

FIG. 3 is a view similar to FIG. 2 showing one preferred embodiment of this invention.

DETAILED DESCRIPTION OF THE PREFERRED EMBODIMENT

Figure 1:
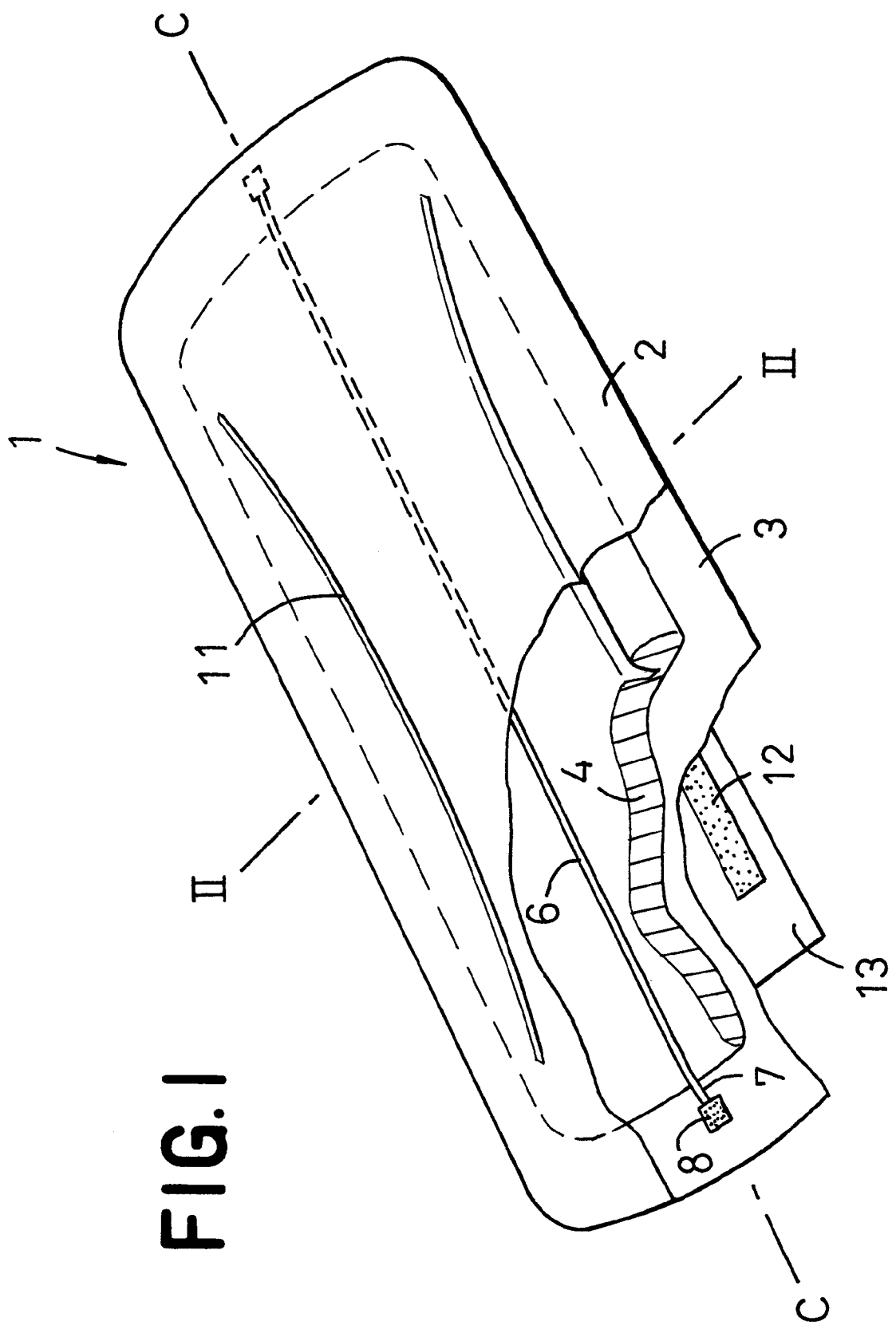
FIG. 1 is a perspective view showing a partially cut away sanitary napkin according to a principle of this invention.

Details of a sanitary napkin according to this invention will be more fully understood from the description given hereunder with reference to the accompanying drawings.

FIG. 1 is a perspective view showing a partially cut away sanitary napkin according to one embodiment of this invention and FIG. 2 is a sectional view taken along a line II—II in FIG. 1. A sanitary napkin 1 is longitudinally larger and basically comprises a liquid-pervious topsheet 2, a liquid-impervious backsheet 3 and a liquid-absorbent core 4 disposed between these two sheets 2, 3. The topsheet 2 and the backsheet 3 are placed upon and bonded to each other along their respective portions extending outward beyond peripheral edges of the absorbent core 4. Between the topsheet 2 and the absorbent core 4, a single elastic member 6 extends under tension along a center line C—C dividing a width of the napkin 1 in two and bonded at longitudinally opposite ends 7 of the elastic member 6 to an inner surface of at least one of the topsheet 2 and the backsheet 3 by means of adhesive agent 8.

In the vicinity of transversely opposite side edges of the napkin 1, the topsheet 2 and the absorbent core 4 are compressed together toward the backsheet 3 to form a pair of grooves 11, 11 extending longitudinally of the napkin 1.

The backsheet 3 is applied on its lower surface with adhesive agent to form three stripe-like fastening zones 12 extending longitudinally of the napkin 1 and are protected with respective release paper sheets 13.

The napkin 1 of such arrangement is longitudinally curved with the topsheet 2 lying inside so as to follow a curvature of an undergarment worn by a wearer, particularly a curvature of the crotch region when the napkin 1 is put on the wearer's body by peeling the release paper sheets 13 off from the respective fastening zones 12 and thereby fastening the napkin 1 to the crotch region of the undergarment. Thereupon, the elastic member 6 contracts and consequently the topsheet 2 is lifted up, as indicated by imaginary lines, into close contact with pudendum of the wearer. Most of menstrual discharge is rapidly absorbed into the napkin 1 through a portion of the topsheet 2 being in close contact with the pudendum of the wearer and, if the amount of discharge is relatively plenty, the excessive amount of menstrual discharge may flow sideways along a sloping surface of the lifted topsheet 2.

However, such excessive amount of menstrual discharge scarcely causes undesirable sideways leakage, since the excessive amount of menstrual discharge flows into the grooves 11 and is effectively prevented thereby from further flowing sideways. In the case of the absorbent core 4 mainly comprising liquid-absorbent fibers, the amount of menstrual discharge flowing along the sloped surface is rapidly absorbed by the absorbent core 4 in the grooves 11 and rapidly diffused longitudinally along the grooves 11 since a fiber density in the grooves 11 is higher than a fiber density in the vicinity of these grooves 11. Leakage of menstrual discharge is prevented still more reliably by such absorptive and diffusive effects of the grooves 11.

FIG. 3 is a view similar to FIG. 2 showing another embodiment of this invention. In this embodiment of the sanitary napkin 1, the absorbent core 4 comprises an upper core 16 and a lower core 17 and a pair of elastic members 6 extend longitudinally of the napkin 1 between the upper and lower cores 16, 17. The upper and lower cores 16, 17 are integrally compressed along the grooves 11 but free to be spaced from each other in their regions defined between the pair of grooves 11. Each of the elastic members 6 has its longitudinally opposite ends 7 extending outward beyond respective longitudinally opposite ends of the upper and lower cores 16, 17 and bonded to the inner surface of at least one of the topsheet 2 and the backsheet 3 (not shown).

When the napkin 1 is longitudinally curved and thereupon the elastic members 6 contract, the topsheet 2 is lifted up together with the upper core 16, as indicated by imaginary lines. With such napkin 1 being in this state, menstrual discharge is more rapidly absorbed through the topsheet 2 than in the case of the napkin 1 shown in FIG. 1, since the upper core 16 remains in close contact with the topsheet 2 even after the latter is lifted up. In this embodiment, the upper and lower cores 16, 17 may be of the same composition. Instead, it is also possible to form the upper core 16 mainly by fluff pulp and to form the lower core 17 by a mixture of fluff pulp and superabsorptive polymer particles.

To exploit this invention, a nonwoven fabric or an apertured plastic film may be used as stock material for the topsheet 2 and a plastic film may be used as stock material for the backsheet 3. The absorbent core 4 may be formed by liquid-absorbent fibers such as the fluff pulp or by a mixture of such fibers and superabsorptive polymer particles. It is also possible to add the fluff pulp or the mixture with liquid-impervious thermoplastic synthetic fibers up to 30% by weight or less. Addition of such thermoplastic synthetic fibers improves a menstrual discharge diffusing ability of the absorbent core which is formed by fluff pulp. For the absorbent core formed by fluff pulp mixed with the thermoplastic synthetic fibers, addition of this thermoplastic synthetic fibers improves a shape holding ability of the absorbent core so far as the absorbent core is heated under pressure so that heat-sealing may occur among the individual thermoplastic synthetic fibers as well as among the individual pulp fibers. The upper core 16 adapted to be vertically movable relatively to the lower core 17 is preferably the absorbent core having its shape holding ability improved in this manner.

The sanitary napkin according to this invention can avoid undesirable sideways leakage of menstrual discharge because of its unique arrangement. Namely, the region of the napkin defined between the pair of grooves longitudinally extending in the vicinity of both side edges, respectively, of the napkin is adapted to protrude and an excessive amount of menstrual discharge will flow along the sloped surface of the protruding region into the respective grooves. The bottom of each groove is formed by a high density liquid-absorbent fibers which can rapidly absorb and diffuse the amount of menstrual discharge having flown thereinto. In this manner, the effect of preventing the menstrual discharge from leaking sideways can be improved.

What is claimed is:

1. A sanitary napkin for absorption and containment of menstrual discharge having a longitudinal center line, said sanitary napkin comprising:

a liquid-pervious topsheet;

a liquid-impervious backsheet;

a liquid-absorbent core disposed between said liquid-pervious topsheet and said liquid-impervious backsheet; and at least one elastic member being provided between said liquid-pervious topsheet and said liquid-impervious backsheet, said at least one elastic member extending adjacent to said longitudinal center line under tension and having longitudinally opposite ends which are bonded to one of said liquid-pervious topsheet and said liquid-impervious backsheet so that said at least one elastic member can be stretched and contracted between said ends, a pair of compressed grooves formed in the vicinity of transversely opposite side edges of said sanitary napkin by compressing said liquid-absorbent core and said liquid-pervious topsheet toward said liquid-impervious backsheet, said pair of compressed grooves extending longitudinally of said sanitary napkin and integrating said liquid-pervious topsheet, said liquid-impervious backsheet, and said liquid-absorbent core so that said liquid-pervious topsheet, said liquid-impervious backsheet, and said liquid-absorbent core are not easily separable from one another in said compressed grooves, portions of said sanitary napkin lying in said compressed grooves having a density which is higher than a density adjacent said compressed grooves, a portion of said sanitary napkin which overlies said at least one elastic member in a thickness direction of the sanitary napkin being formed separably from a portion of said liquid-absorbent core which underlies said at least one elastic member in said thickness direction of the sanitary napkin so that said portion of said sanitary napkin which overlies said at least one elastic member and which is defined between said compressed grooves moves upward and closely contacts a wearer's pudendum as said sanitary napkin is longitudinally curved.

2. A sanitary napkin according to claim 1, wherein said at least one elastic member is disposed between said liquid-pervious topsheet and an upper surface of said liquid-absorbent core.

3. A sanitary napkin according to claim 1, wherein said absorbent core comprises an upper layer portion and a lower layer portion between which said elastic member is disposed.

4. A sanitary napkin according to claim 1, wherein said at least one elastic member comprises a single elastic member that extends along said longitudinal center line.

5. A sanitary napkin according to claim 1, wherein said at least one elastic member comprises a pair of elastic members that extend adjacent opposite sides of said longitudinal center line.

6. A sanitary napkin according to claim 1, wherein said at least one elastic member extend parallel to said longitudinal center line.

* * * * *

UNITED STATES PATENT AND TRADEMARK OFFICE
CERTIFICATE OF CORRECTION

PATENT NO. : 6,410,822 B1
DATED : June 25, 2002
INVENTOR(S) : Satoshi Mizutani

It is certified that error appears in the above-identified patent and that said Letters Patent is hereby corrected as shown below:

<u>Title page,</u>
Item [57], ABSTRACT,
Line 5, before "topsheet" add -- the --
Line 6, before "absorbent" add -- the --

<u>Column 4,</u>
Line 32, change "separably" to -- separately --
Line 44, before "absorbent" add -- liquid --
Line 45, before "elastic" add -- at least one --
Line 52, change "extend" to -- extends --

Signed and Sealed this

Seventeenth Day of December, 2002

JAMES E. ROGAN
*Director of the United States Patent and Trademark Office*